United States Patent
Testoni (10) Patent No.: US 7,202,475 B1
(45) Date of Patent: Apr. 10, 2007

(54) RAPID DEFECT COMPOSITION MAPPING USING MULTIPLE X-RAY EMISSION PERSPECTIVE DETECTION SCHEME

(75) Inventor: Anne L. Testoni, Bolton, MA (US)

(73) Assignee: KLA-Tencor Technologies Corporation, Milpitas, CA (US)

(*) Notice: Subject to any disclaimer, the term of this patent is extended or adjusted under 35 U.S.C. 154(b) by 199 days.

(21) Appl. No.: 10/796,577

(22) Filed: Mar. 8, 2004

Related U.S. Application Data (60) Provisional application No. 60/453,156, filed on Mar. 6, 2003.

(51) Int. Cl.
*H01J 37/30* (2006.01)
*G01N 23/00* (2006.01)
*G21K 7/00* (2006.01)

(52) U.S. Cl. .................. 250/310; 250/307; 702/40; 702/134

(58) Field of Classification Search .................. None
See application file for complete search history.

(56) References Cited

U.S. PATENT DOCUMENTS

| | | | | |
|---|---|---|---|---|
| 3,030,507 A | * | 4/1962 | Khol | 378/72 |
| 3,046,399 A | * | 7/1962 | Ladell | 378/49 |
| 3,213,278 A | * | 10/1965 | Spielberg | 378/49 |
| 3,663,812 A | * | 5/1972 | Koenig et al. | 378/49 |
| 4,472,825 A | * | 9/1984 | Jenkins | 378/49 |
| 4,885,465 A | * | 12/1989 | Nagatsuka et al. | 250/310 |
| 4,959,848 A | * | 9/1990 | Parobek | 378/46 |
| 5,187,727 A | * | 2/1993 | Vogler et al. | 378/50 |
| 5,237,598 A | * | 8/1993 | Albert | 378/98.6 |
| 5,457,725 A | * | 10/1995 | Sato | 378/49 |
| 5,594,246 A | * | 1/1997 | Sudo et al. | 250/310 |
| 5,703,361 A | * | 12/1997 | Sartore | 250/310 |
| 5,866,903 A | * | 2/1999 | Morita et al. | 250/310 |
| 5,877,498 A | * | 3/1999 | Sugimoto et al. | 250/310 |
| 6,407,386 B1 | | 6/2002 | Dotan et al. | |
| 6,448,556 B1 | * | 9/2002 | Cowley et al. | 250/311 |
| 6,664,541 B2 | * | 12/2003 | Nasser-Ghodsi et al. | 250/310 |
| 6,810,105 B2 | * | 10/2004 | Nasser-Ghodsi et al. | 378/44 |
| 6,855,930 B2 | * | 2/2005 | Okuda et al. | 250/310 |
| 6,924,484 B1 | * | 8/2005 | Wang et al. | 250/310 |
| 2003/0223536 A1 | * | 12/2003 | Yun et al. | 378/45 |

OTHER PUBLICATIONS

Serulink, "Defect Topographic Maps Using a Non-Lambertian Photometric Stereo Method", Applied Materials, Israel Ltd., Jul. 2002.

* cited by examiner

*Primary Examiner*—Nikita Wells
(74) *Attorney, Agent, or Firm*—Beyer Weaver LLP (57) ABSTRACT

Disclosed are methods and apparatus for characterizing defects by using X-ray emission analysis techniques. The X-rays are emitted in response to an impinging beam, such as an electron beam, directed towards the sample surface where a defect resides. It may also be used to help determine where the void(s) are with respect to the interconnect structure. Methods disclosed are for spatially locating defects in or on integrated circuits. Also disclosed are methods for identifying the elemental composition of defects and spatially locating different elemental components of defects.

49 Claims, 10 Drawing Sheets

RAPID DEFECT COMPOSITION MAPPING USING MULTIPLE X-RAY EMISSION PERSPECTIVE DETECTION SCHEME

CROSS REFERENCE TO RELATED PATENT APPLICATION

This application claims priority of U.S. Provisional Application No. 60/453,156 filed on Mar. 6, 2003, entitled RAPID DEFECT COMPOSITION MAPPING USING MULTIPLE X-RAY EMMISION PERSPECTIVE DETECTION SCHEME, by Anne Testoni which is incorporated herein by reference in its entirety for all purposes.

This application is related to U.S. patent application Ser. No. 10/691,940, filed on Oct. 22, 2003, entitled VOID CHARACTERIZATION IN METAL INTERCONNECT STRUCTURES USING X-RAY EMISSION ANALYSES, by Yeishin Tung and Anne Testoni which is incorporated herein by reference in its entirety for all purposes.

FIELD OF THE INVENTION

The present invention relates generally to inspection of semiconductor devices for the purpose of identifying defects thereon. Additionally, it relates to X-ray emission analysis techniques for identifying and spatially locating defects found in or on integrated circuit devices.

BACKGROUND OF THE INVENTION

Semiconductor defects may include structural flaws, residual process material and other surface contamination, which occur during the production of semiconductor wafers. Defects can be introduced to a wafer at any process step in wafer production. For example, a particle defect may originate from contamination during a deposition process or it may be introduced to the wafer due to exposure during a wafer transfer from one process chamber to another. As another example, a scratch defect may occur due to abrasive polishing during a chemical mechanical planarization process, or it may occur due to faulty cleaning process or it may occur from operator error during wafer handing. Since defects can have a similar appearance but originate from different process steps, it can be difficult to find root causes of the defects, such as a faulty process. It is also important to know where the defect is located with respect the different process layers of the semiconductor wafer, which may also aid determination of the root cause of the defect.

To help detect and locate defects, a class of instruments called inspection tools is used. Inspection tools inspect the wafers at various critical points between process steps in wafer production. Such instruments scan wafer surfaces using a variety of techniques and detect and record the location of anomalies. Typically, these techniques involve directing a light or electron beam towards the surface of the semiconductor where the defect is, and detecting the resultant light reflected off or electrons emitted from the sample. The reflected light or emitted electrons may then be used to generate a target image of the surface of the semiconductor. Differences between the target image and a reference image (which is known to contain no defects) are determined and, when the differences are above a predetermined threshold, it may be determined that a defect exist.

One problem that occurs with existing inspection technologies is they do not always accurately locate where the defects are in relation to the different layers of the semiconductor. This is because many inspection tools collect one or two dimensional images of defects. For example, most electron beam inspection tools detect emitted electrons using one detector at one angle in relation to the sample surface. The data is collected from one perspective and results in a one dimensional representation or, at best, a flat two dimensional image, much like a common camera photograph. The one and two dimensional representations alone do not show depth. When viewing the image, one may not be able to distinguish between an indentation that recesses below the wafer surface and a bump or particle that protrudes above the wafer surface. If the defect is particle, it may occlude or shadow another defect behind it. Also, one will not know if the defect simply lies on the surface, extends into other process layers or spans over multiple layers.

The spatial location of defects can be vital information for engineers to accurately determine the root causes of defects. For example, if a particle is introduced in a deposition chamber during a deposition process, the particle may be embedded with the material of the deposition process layer. Whereas, if the particle was introduced after the deposition process, the particle will likely not be embedded within the material of the particular deposition process layer but rather reside on top of the wafer surface or within another process layer besides the particular deposition layer. Likewise, it is important for engineers to know the spatial location of other defects such as scratches, indentations, bumps and other irregularities in relation to the various layers of the wafer structure.

These are only a few examples of the types of puzzles that engineers must solve everyday to insure efficient, cost effective and quality wafer production.

Accordingly, there is a need to spatially resolve the location of defect that may reside in or on integrated circuit product devices or wafers.

SUMMARY

In general terms, the present invention provides methods and apparatus for localizing and characterizing one or more defects by analyzing the X-ray count of one or more emitted X-ray species emitted from the semiconductor wafer and defect(s) under test in response to a impinging beam, such as an electron beam, directed towards the sample surface in the area where the defect(s) reside. Specifically, this analysis may be used for spatially resolving the location of a defect with respect to the semiconductor wafer using multiple perspective X-ray emission detection. Defects which can be inspected using the methods of the invention include particles, flakes, bumps, pits, voids, recesses, scratches and other irregularities or undesirable features that can exist in or on wafers.

By directing a beam of appropriate energy toward the wafer sample surface in the area where a defect resides, a certain sample volume of the wafer sample with defect will generate X-rays. Preferably, the defect that is being inspected resides within this sample volume. The X-rays will radiate from the volume within the wafer sample and some of the X-rays will be emitted from the wafer sample surface. These emitted X-rays are characteristic of composition of the wafer sample and of the defect. If the emitted X-rays are detected at two or more perspectives or angles, the defect can be spatially resolved and a three dimensional image of the defect in or on the wafer sample can be produced. Combining the X-ray data from at least two X-ray emission energy spectra can generate the image. The more perspectives or angles used to detect emitted X-rays, the better the confidence of the spatially resolved data and three dimensional images.

A number of embodiments of the invention are based on how the detector or detectors are oriented with respect to the wafer surface so that emitted X-rays from at least two perspectives can be achieved. In a preferred embodiment, the emitted X-rays are detected using a plurality of detectors positioned at a plurality of angles with respect to the wafer surface. In this embodiment, the emitted X-rays can be detected simultaneously. In other embodiments, one detector is used to collect the emitted X-rays from a plurality of perspectives by either moving the detector with respect to the wafer surface or by tilting the wafer with respect to the detector position between samplings. In these embodiments, the emitted X-rays are detected at different sampling times. Any number of samplings and perspectives can be performed. In another embodiment, one detector is used to collect the emitted X-rays from a plurality of perspectives by using a detector capable of collecting X-rays emitted from the sample surface at least two significantly different angles. In this embodiment, the emitted X-rays can be detected simultaneously.

A number of embodiments of the invention are based on the methods in which the beam can be used to impinge the wafer sample. In a few embodiments, the beam is stepped over the area where the defect resides. In a preferred embodiment, the beam is stepped in a grid pattern or configuration over the area where the defect resides. The stepping pattern of the beam can include any number of inspection points, preferably to fully sample the volume of the wafer wherein/whereon the defect resides. In another embodiment, the beam is rastered or scanned over the area where the defect resides. In another embodiment, the beam impinges the area where the defect resides at a single point.

A few embodiments of the invention are based on the type of beam used to cause the generation of X-rays from the wafer sample. In a preferred embodiment, an e-beam is used to impinge the wafer. The e-beam is preferably sufficiently focused to resolve even small defects. The e-beam has preferably high enough energy to travel through the different layers of a typical semiconductor film stack and cause X-ray emission from the defect and surrounding wafer sample. In another embodiment, a focused ion beam is used to impinge the wafer.

Methods of the present invention can be used to inspect defects in a number of different types of semiconductor wafer devices, including devices comprised of aluminum, copper, silicon, silicon dioxide, low k dielectrics, tantalum, titanium, tungsten, silicon nitride, tantalum nitride and other materials found in semiconductor wafers. In one embodiment, the wafer sample is comprised of copper surrounded by dielectric material, such as damascene devices. In this embodiment, detecting and collecting the copper Kα and copper Lα X-rays emitted from the sample, and by taking various ratios of the copper Kα and copper Lα X-rays, one can characterize the semiconductor material surrounding the defect. One can also detect and collect X-ray emission from other elemental species emitted from the sample, such as those from the defect.

These and other features of the present invention will be presented in more detail in the following specification of the invention and the accompanying figures, which illustrate by way of example the principles of the invention.

DETAILED DESCRIPTION OF SPECIFIC EMBODIMENTS

Introduction

In the following description, numerous specific details are set forth in order to provide a thorough understanding of the present invention. The present invention may be practiced without some or all of these specific details. In other instances, well known process operations have not been described in detail to not unnecessarily obscure the present invention. While the invention will be described in conjunction with the specific embodiment, it will be understood that it is not intended to limit the invention to the embodiment. On the contrary, it is intended to cover alternatives, modifications, and equivalents as may be included within the spirit and scope of the invention as defined by the appended claims.

A "semiconductor wafer" or "wafer" is a semiconductor substrate at any state of manufacture in the production of integrated circuits. One standard semiconductor wafer described in this invention is 200 mm in diameter, 0.75 mm thick (see e.g., SEMI Specification M1-0298). Of course, semiconductor wafers of other dimensions, such as a standard 300 mm diameter silicon wafer, can also be processed in accordance with this invention. Note that standard specifications for a 300 mm diameter wafer may be found in SEMI Specification M1.15-0997. As used herein, "wafer surface" refers to any semiconductor wafer surface whereby an inspection for defects is performed. Wafer surfaces include semiconductor wafer surfaces in various states of manufacture. During wafer production, the wafer surface is typically inspected for defects after critical process steps, which critical steps are well known to those skilled in the art.

Generally, the present invention applies to inspecting defects in or on wafers using X-ray emission techniques. In general terms, X-ray emission analyses involve characterizing the composition of a sample by exciting the atomic core electrons within a sample and analyzing the resulting emitted X-rays. In the present invention, excitement of the atomic core electrons is achieved by bombarding the sample with a focused electron beam (e-beam), although other techniques of inducing X-ray emission such as a focused ion beam can be used. Upon sample bombardment, a transfer of energy occurs which excite the atomic core electrons into different electronic energy levels. Once in this excited state, the atoms have two possible modes of relaxation: emission of X-rays, or emission of Auger electrons.

Figure 1:
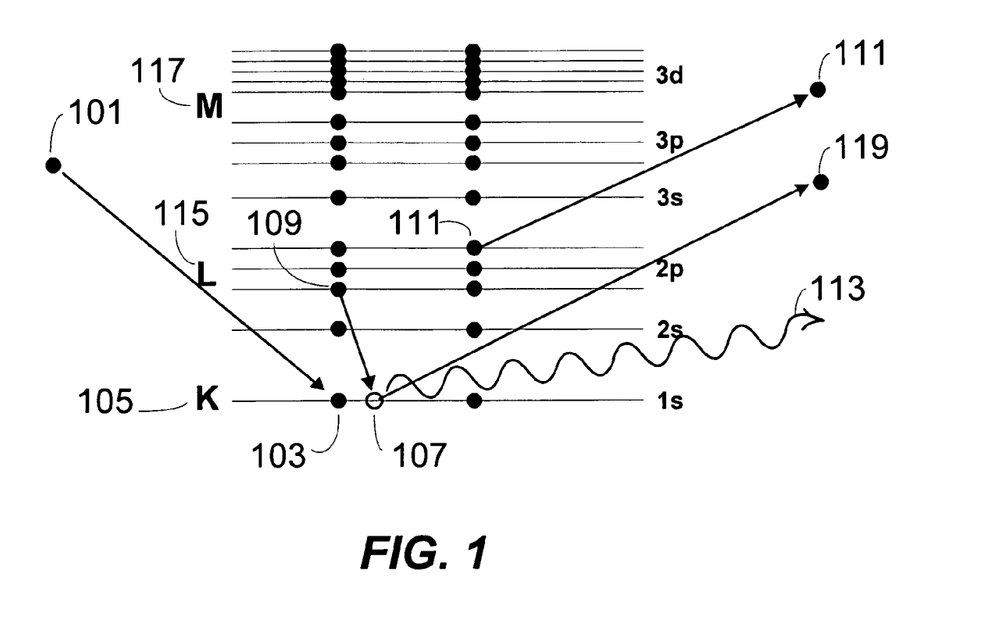
FIG. 1 is a diagram of a Bohr model of an atom showing electronic transitions during Auger electron emission and X-ray emission competing processes.

To illustrate these two possibilities, FIG. 1 illustrates a Bohr model of an atom with three electronic energy levels K, L and M (105, 115 and 117, respectively), with electrons in K having greater electronic binding energy than those in L, and electrons in L having greater binding energy than those in M. An incident electron 101 strikes an atom with enough energy to displace an atomic core electron 103, causing the ejection of a secondary electron 119 and producing a core hole or vacancy 107. With the vacancy in the core energy level, the atom is energetically unstable. The most probable stabilization mechanism is filling the vacancy with another electron in a higher energy level 109. That is, a second electron falls from a higher level into the vacancy with release of energy. The resulting energy may then be carried off by one of two mechanisms: Auger electron emission or X-ray emission. In Auger electron emission, the resulting energy is carried off when an Auger electron 111 from a higher energy level is ejected. In X-ray emission, the resulting energy is carried off in the form of emitted X-rays 113, leaving an ionized atom. Auger electron emission and X-ray emission are competitive processes.

The present invention pertains to the detection and analysis of X-ray emissions of a sample in accordance with the above description. Each element has its own characteristic electronic energy configurations and its own characteristic X-ray emissions. For example, copper has two dominant characteristic X-ray emissions: an L$\alpha$ emission (emitted when an electron falls into the L electronic energy level) with an associated energy of about 0.93 kilo electron volts (keV); and a K$\alpha$ emission (emitted when an electron falls into the K electronic energy level) with an associated energy of about 8.04 keV. Other elements will have their own characteristic associated energy transitions and X-ray emissions.

Figure 2:
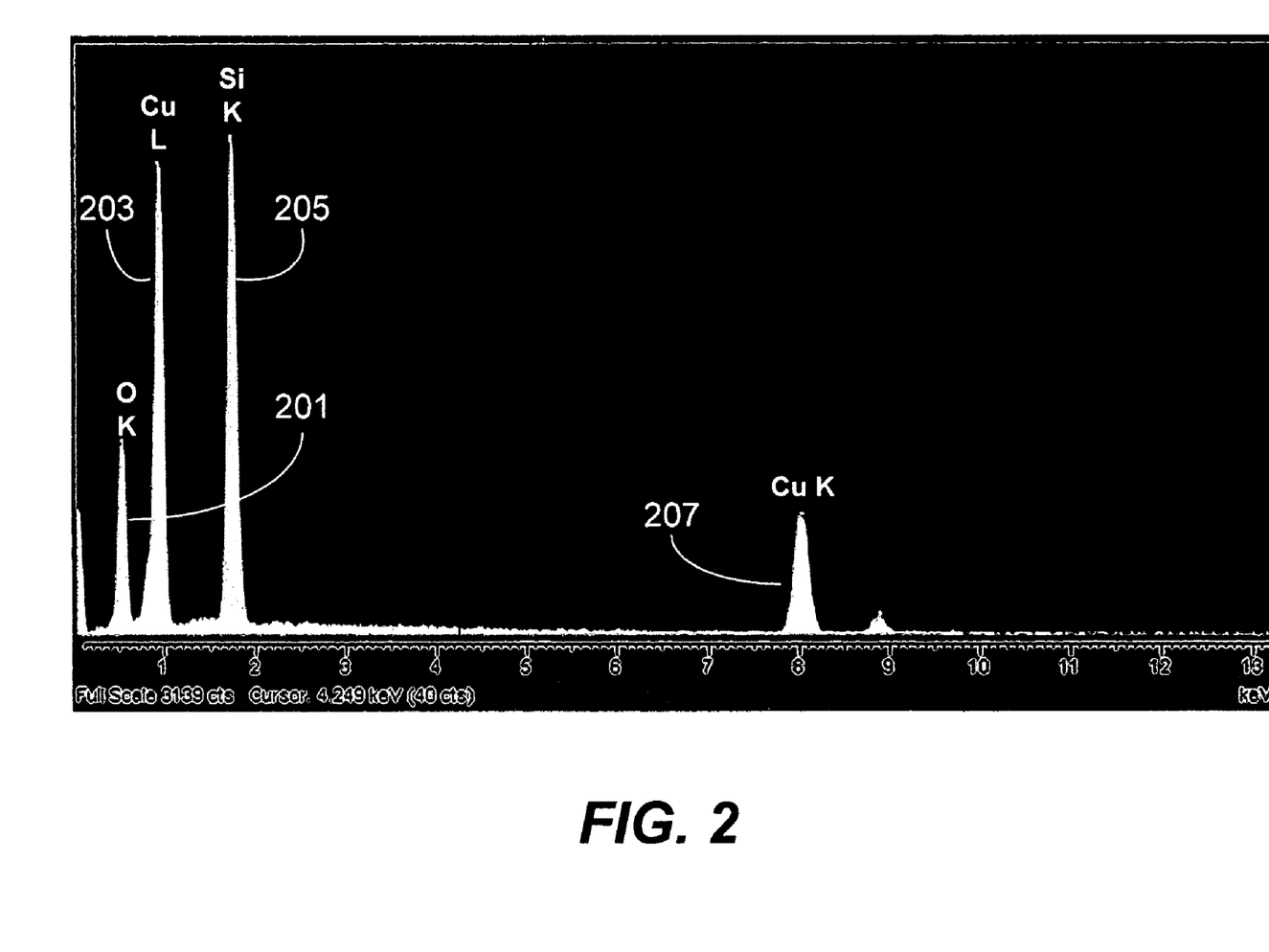
FIG. 2 is an X-ray emission spectrum from a copper semiconductor integrated device sample.

The X-ray emissions of a sample can be collected in the form of an X-ray emission energy spectrum. For example, FIG. 2 is an X-ray emission energy spectrum from a copper interconnect structure in an integrated circuit. The horizontal axis represents energy in keV and the vertical axis is the relative intensity. The oxygen K$\alpha$ (O K$\alpha$) peak 201 has an energy of about 0.93 keV. The copper L$\alpha$ (Cu L$\alpha$) peak 203 has a larger intensity than the O K$\alpha$ and has an energy of around 1 keV. The silicon K$\alpha$ (Si K$\alpha$) peak 205 has a larger intensity than the Cu L$\alpha$ and O K$\alpha$ peaks and has an energy of almost 2 keV. The copper K$\alpha$ peak (Cu K$\alpha$) 207 has a lower intensity than the O K$\alpha$, Cu L$\alpha$ and Si K$\alpha$ peaks and has an energy of about 8.04 keV. The relative intensities of the peaks in this X-ray spectrum can be compared to spectra of the pure elements or other samples of known composition to determine the elemental composition and amounts of each element within the sample.

Therefore, if the atoms of a defect and the surrounding material are sufficiently excited to emit X-rays and these X-rays are detected, the elemental composition of the defect and surrounding material can be determined. One can use standard techniques to display an image, also called a map, of the wafer with the defect showing elemental compositions. This will be discussed further below.

Figure 3:
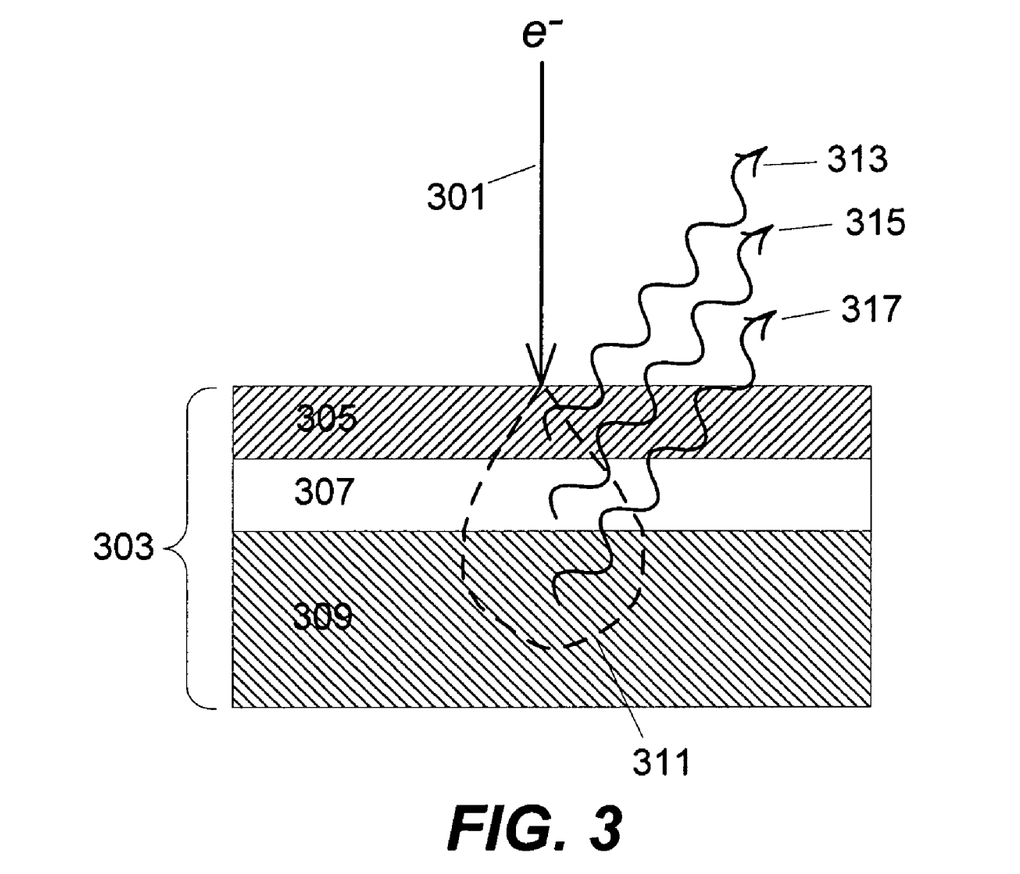
FIG. 3 illustrates a cross section of a semiconductor specimen with an electron beam incident upon a sample, resulting in X-rays being emitted by various layers of the sample material.

In a preferred embodiment of the invention, X-ray emission is induced with an electron beam (e-beam). If the e-beam is of sufficient energy, bombardment of a sample will result in an approximately "teardrop" shaped region, or volume, of excitation within the sample. This teardrop volume is depicted in FIG. 3. The figure illustrates a cross sectional view of a sample integrated circuit stack 303 composed of layers of copper 305 and dielectric material 307 over a silicon substrate 309 being bombarded by a focused e-beam 301. The e-beam bombardment results in a teardrop shaped volume 311 wherein electron trajectories travel, thereby causing X-ray emission from the copper, dielectric and silicon layers in the stack (313, 315 and 317, respectively). This teardrop region is three-dimensional in that it covers a teardrop shaped volume within the sample. An X-ray detector can detect emitted X-rays from this teardrop region. In one embodiment, at least two detectors are used so that spatial information can be obtained. This and other variations will be described in detail further.

Note that the incident e-beam will preferably have a high enough energy to generate X-rays from the surface of the wafer as well as from different layers of the film stack. This e-beam energy will depend on the sample composition and thickness and on how deeply the defect to be examined lies or how deeply a defect can possibly lie.

Defects in integrated circuits can be very small. Therefore, to characterize such small defects, the e-beam diameter is preferably sufficiently focused to resolve them. If a defect is large, the e-beam may be rastered or stepped over the general area where the defect resides. In a preferred embodiment, the e-beam is stepped in a grid pattern over the area where the defect resides. This stepping technique will be described later.

Multiple Perspective X-Ray Detection

As stated previously, X-ray emissions techniques can be used to spatially resolve the location of defects. That is, X-ray emissions techniques can be used to determine the location of defects in three dimensions in relation to the different process layers of the wafer. Some aspects of these techniques will now be described. Typical defects include particles, flakes, bumps, pits, voids, recesses, scratches and other irregularities or undesirable features that can exist in or on wafers. To simplify discussions, reference will be made to a specific example, a particle defect. However, it should be noted that the following techniques can be used to inspect any type of wafer defect, such as voids, recesses, scratches, etc.

Figure 4A:
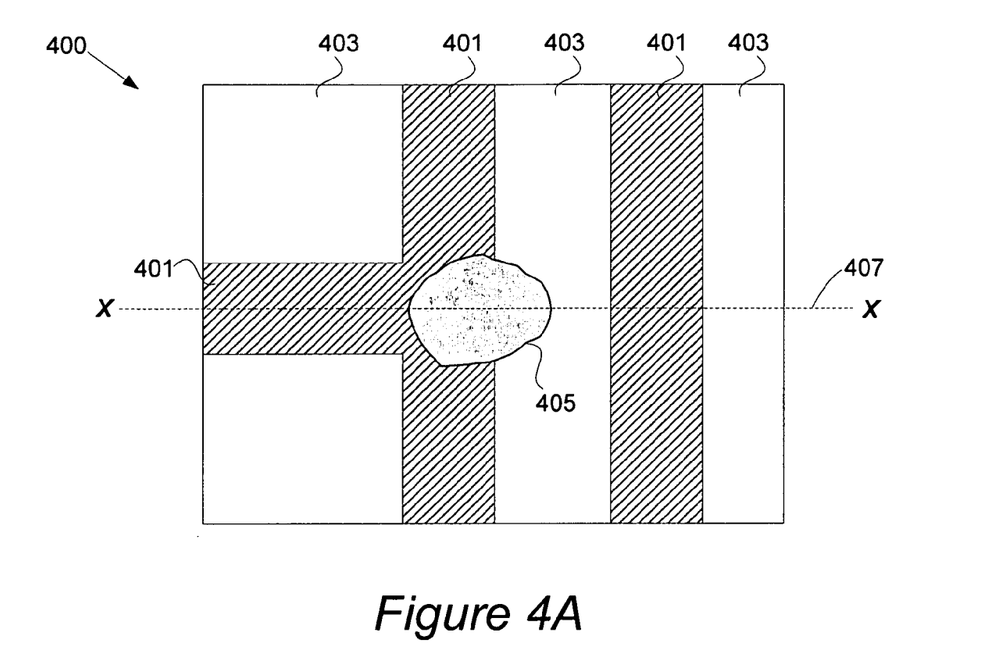
FIG. 4A illustrates a top view of a section of a semiconductor wafer with a defect.

FIG. 4A depicts a top view of a portion of a semiconductor wafer sample 400 containing a particle defect 405.

Figure 4B:
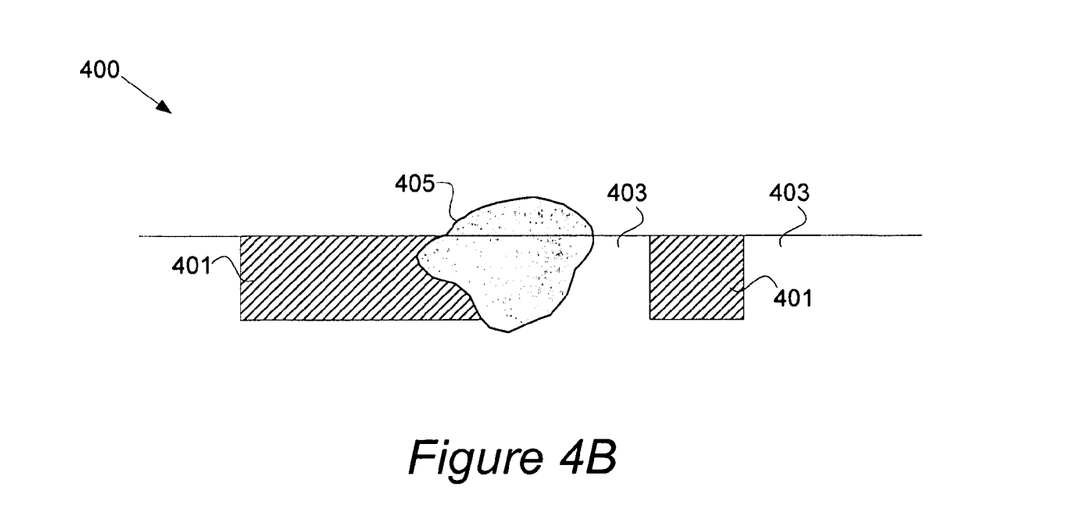
FIG. 4B illustrates a cross sectional view of the semiconductor wafer of FIG. 4A.

The defect 405 lies partially on top of a conductive line made of copper 401 and partially on surrounding dielectric insulation material 403. Traditional two dimensional inspection techniques such as scanning e-beam imaging techniques would typically show an image similar to this top view of the defect, with no three dimensional orientation. FIG. 4B depicts a cross sectional view of the same portion of wafer 400 of FIG. 4A, cross sectioned at line 407. This cross sectional view shows that defect 405 not only resides on top of copper lines 401 and dielectric 403, but also under the wafer surface and into the surrounding copper lines 401 and dielectric 403. Techniques in the present invention are used to resolve the three dimensional spatial relationship between the defect 405 and the wafer 400.

As discussed previously, in a preferred embodiment, an e-beam is used to induce X-ray emissions from the wafer sample. In addition, there are numerous methods of detecting the emitted X-rays in ways that allow for spatially resolving the location of defects. In general terms, the X-ray emissions from various portions of the sample are detected and then converted into a gray scale or color image, where each gray level or color of the image corresponds to a particular intensity level at a particular energy level within a particular sample area. For example, the peak intensity values for copper may correspond to the color blue, so that a copper particle defect has a blue appearance within the image generated from the X-rays emitted from such defect.

FIGS. 5A–5D illustrate three different detector configurations in accordance with the present invention. Note that the illustrations of FIGS. 5A–5D are not to scale. That is, the wafer and defect are shown as much larger than they would be in reality in relation to the size and locations of the detectors. This is to better illustrate aspects of the invention. FIGS. 5A–5D will now be described in detail.

Figure 5A:
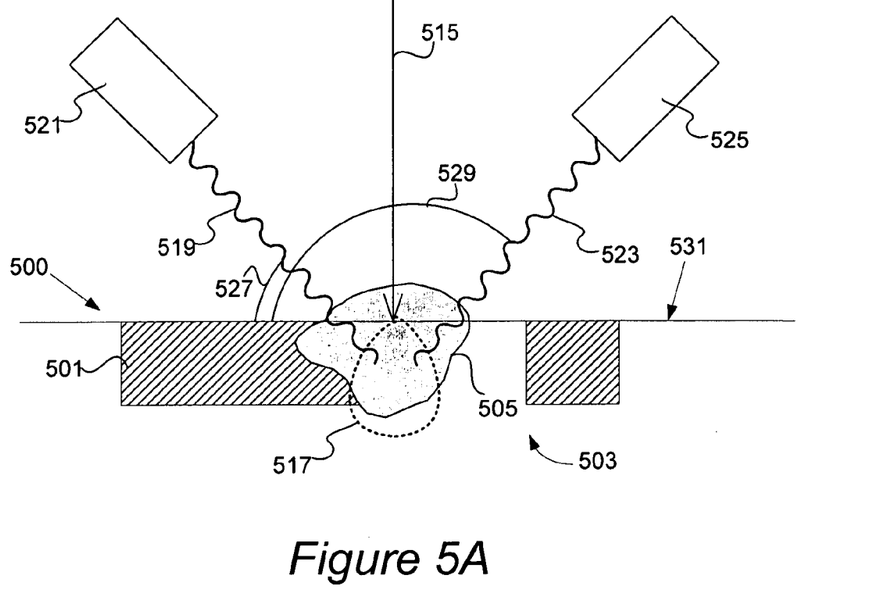
FIG. 5A illustrates a cross sectional view of a semiconductor wafer with an electron beam incident upon the sample and emitted X-rays being detected by two detectors.

FIG. 5A depicts the wafer sample 500 with an e-beam 515 directed at the defect 505. This causes a volume of the sample 517 comprising part of the defect 505, copper 501 and dielectric 503 to emit X-rays 519 and 523. Note that in reality, X-rays are emitted randomly in all directions from the volume, and from all regions within the volume 517. Some of the emitted X-rays are blocked by atoms within the sample, scatter within the sample and do not get emitted from the surface. Others X-rays do not get scattered and are emitted from the surface of the sample. Detectors that are placed above the wafer surface 531 can detect some of these X-rays, depending on the angles of the emitted X-rays and the angles of the detectors with respect to the wafer surface 531.

FIG. 5A shows X-rays 519 emitted from the wafer 500 with defect 505 and detected by a detector 521, which is placed at an angle 527 with respect to the wafer surface 531. X-rays 523 are detected by a detector 525, which is placed at a different angle 529 with respect to the wafer surface 531. In this example, angle 527 is 45 degrees and angle 529 is 135 degrees with respect to the wafer surface 531. Since emitted X-rays are being detected at two different angles, this provides two different X-ray spectra. For each detected spectra, each intensity peak at each different energy level is translated into a different color or gray level within an image of the wafer 500 with defect 505. These two images generated from the two different X-ray spectra can then be combined using any of a number of standard techniques to create a three dimensional image, or map. One of these techniques will be described later. If the detector angles 527 and 529 are situated to "view" the defect 505 at sufficiently different perspectives, the resultant combined image will show that the defect 505 not only lies on top of the wafer 500, but also within the copper lines 501 and dielectric 503. Of course, any number of detectors can be used to collect any number of X-ray maps that may later be combined to one or several images.

Another advantage of using multiple detectors is that more data can be collected when compared to using only one detector in the same amount of sampling time. For example, if one is using two detectors, twice as much data is collected per e-beam sampling compared to using only one detector, thereby increasing the confidence of the collected data. This advantage can be employed in several applications. One application is to reduce the sampling time for an inspection. For example, if two detectors are used, the sampling time can theoretically be reduced in half while still collecting the same amount of data as when using one detector. This can be useful in a production environment when it is important to reduce the duration of any steps in the manufacturing process. Another application of this embodiment is to keep the sampling time the same but to collect more data, thereby improving the signal to noise ratio (S/N). This can be useful when accurate characterization and localization of a defect is necessary.

Figure 5B:
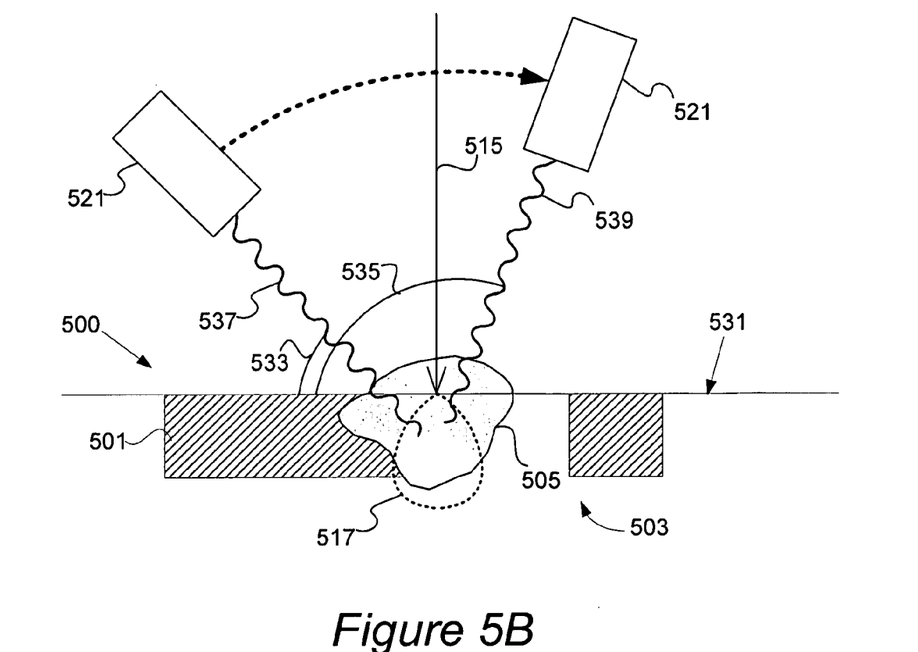
FIG. 5B illustrates a cross sectional view of a semiconductor wafer with an electron beam incident upon the sample and emitted X-rays being detected by one detector at two different detector positions.
Figure 5C:
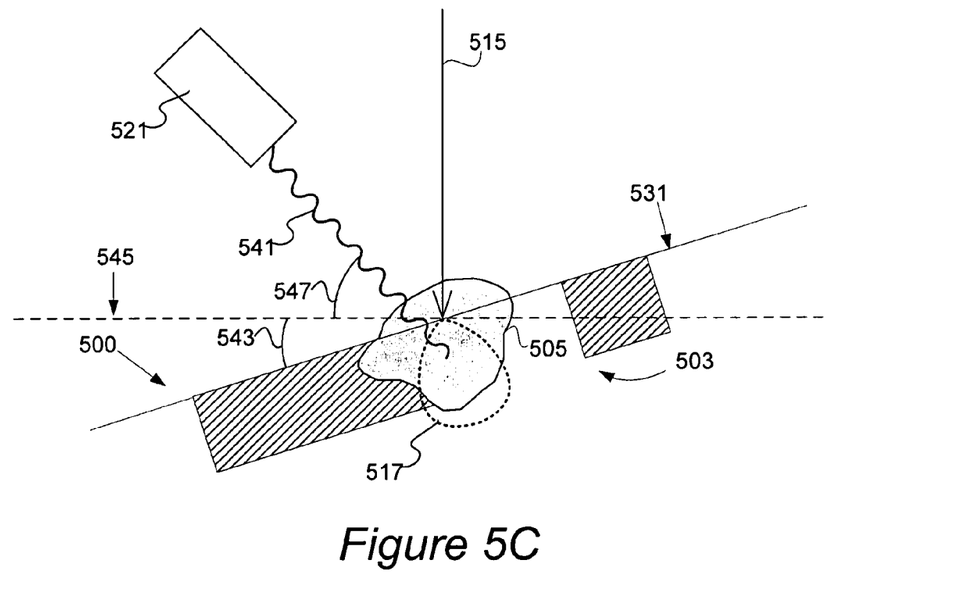
FIG. 5C illustrates a cross sectional view of a semiconductor wafer with an electron beam incident upon the sample and emitted X-rays being detected by one detector while the wafer is tilted.
Figure 5D:
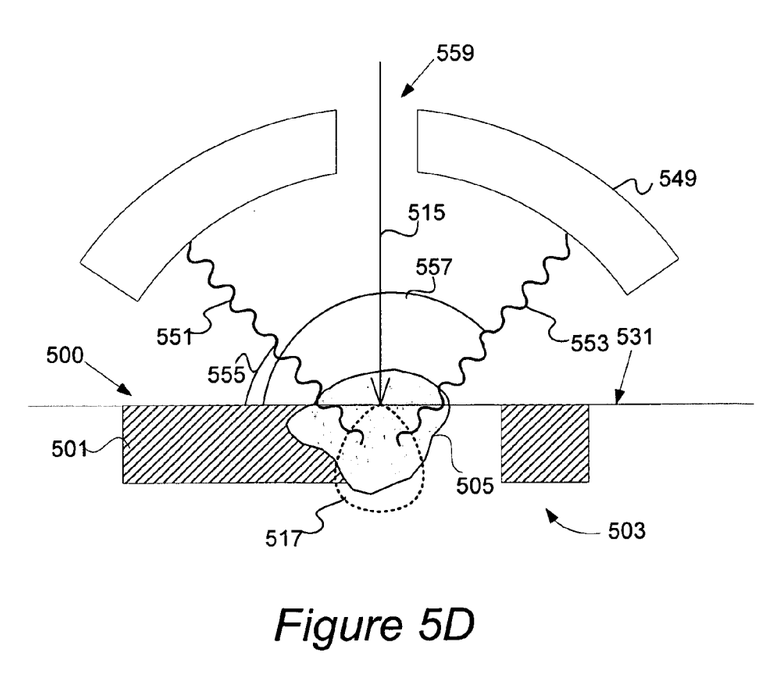
FIG. 5D illustrates a cross sectional view of the semiconductor wafer with an electron beam incident upon the sample and emitted X-rays being detected by one detector that detects X-rays at a number of different angles.

In other embodiments of the invention, one detector can be used to collect emitted X-rays from more than one angle of perspective with respect to the wafer surface. FIGS. 5D–5F illustrate some examples of this. FIGS. 5B and 5C illustrate two examples where one detector is used and either the wafer sample or the detector is moved between e-beam samplings so that more than one angle of perspective can be achieved. FIG. 5D illustrates an example where one detector that is capable of detecting emitted X-rays from a number of significantly different angles is used to resolve spatial information. These examples will now be described in detail.

FIG. 5B shows X-rays 537 emitted from wafer 500 and defect 505 and detected by detector 521, which is placed at an angle 533 with respect to the wafer surface 531. In this example, angle 533 is 45 degrees with respect to the wafer surface 531. The e-beam is turned on and X-rays are detected at this 45 degrees perspective. After this first e-beam sampling, the detector 521 is then moved to another angle 535 with respect to the wafer surface 531. In this example, angle 535 is 110 degrees with respect to the wafer surface 531. Any suitable movement mechanism, such as a motor, may be used to position the detector 521. The e-beam is then turned on again for a second sampling and the resultant emitted X-rays 539 are detected at this 110 degrees perspective by the same detector 521. The images generated from the X-ray data from both of these e-beam samplings are then combined using methods described previously to spatially resolve the defect. If one wants to collect data from different angles, the detector 521 can be positioned to any number of different angles with respect to the wafer surface 531.

FIG. 5C shows X-rays 541 emitted from wafer 500 and defect 505 and detected by detector 521. As shown, the detector 521 is placed at an angle 547 with respect a plane 545 that is perpendicular to the impinging e-beam 515. The wafer 500 is also tilted at an angle 543 with respect to the e-beam perpendicular plane 545. In this example, angle 547 is 45 degrees and angle 543 is 25 degrees with respect to the e-beam perpendicular plane 545. Therefore, the angle of perspective from which detector 521 detects X-rays is 70 degrees (angle 547 plus angle 543). The e-beam is turned on and X-rays are detected at this 70 degrees perspective. After this first e-beam sampling, the wafer 500 is then tilted to another angle with respect to the e-beam perpendicular plane 545. Note that the tilting of wafer 500 to a different angle is not shown in FIG. 5C. The e-beam is then turned on again for a second sampling at this second angle of perspective by the same detector 521. The images generated from the X-ray data from both of these e-beam samplings are then combined using methods described previously to spatially resolve the defect. If one wants to, collect data from different angles, the wafer 500 can be tilted to any number of different angles with respect to the e-beam perpendicular plane 545.

In other embodiments, one detector can be used to detect emitted X-rays from more than one angle of perspective. For example, FIG. 5D shows such a system with such a detector 549. Detector 549 is able to detect X-rays over a large enough radial area so that X-rays at various significantly different angles detected so as to spatially resolve defects. For example, detector 549 can detect X-rays 551 emitted at angle 555 and X-rays 553 emitted at angle 557 with respect to the wafer surface 531. In this example, there is a hole 559 in the detector 549 in the region where the e-beam 515 is directed through to reach the wafer 500. As with the multiple detector embodiment of FIG. 5A, this type of detector will allow for the collection of X-rays at different angles at the same time.

E-Beam Sampling Methods

As mentioned previously, preferred methods of sampling the wafer and defect include impinging the area of the wafer in which the defect resides with an e-beam. There exist many different methods for using an e-beam to inspect wafers. Three general techniques that can be used in accordance with the invention will now be described. Note that the e-beam techniques described can also be applied to methods for using other charged particle beams such as focused ion beams in accordance with the present invention.

A first method is to simply direct the e-beam towards the wafer surface at one point for a certain time until X-rays are caused to be emitted from the sample in response to the e-beam. This method is the simplest way of inspecting the wafer. The inspection area of the wafer is limited by the size of the e-beam diameter and the detected X-rays are limited by the number of X-rays emitted from the excited volume of sample (see FIGS. 5A–5D).

A second method of using an e-beam is rastering, or scanning, the e-beam over an inspection area of the sample. The e-beam is scanned in a continuous side-to-side fashion over the inspection area. The e-beam movement is controlled using electro-optical techniques and the e-beam is kept on during the time in which the sample is being rastered. Rastering is typically done over a short period of time and typically covers only a small area. Typically, e-beam rastering is done in conjunction with e-beam positional monitoring so that the area which is scanned can be transferred into a two dimensional image. Note that this method alone does not allow for three dimensional spatial resolution. To do this, the emitted X-ray must also be detected using a multiple perspective technique as described above. E-beam rastering is a commonly used method because of its short sampling time.

Figure 6A:
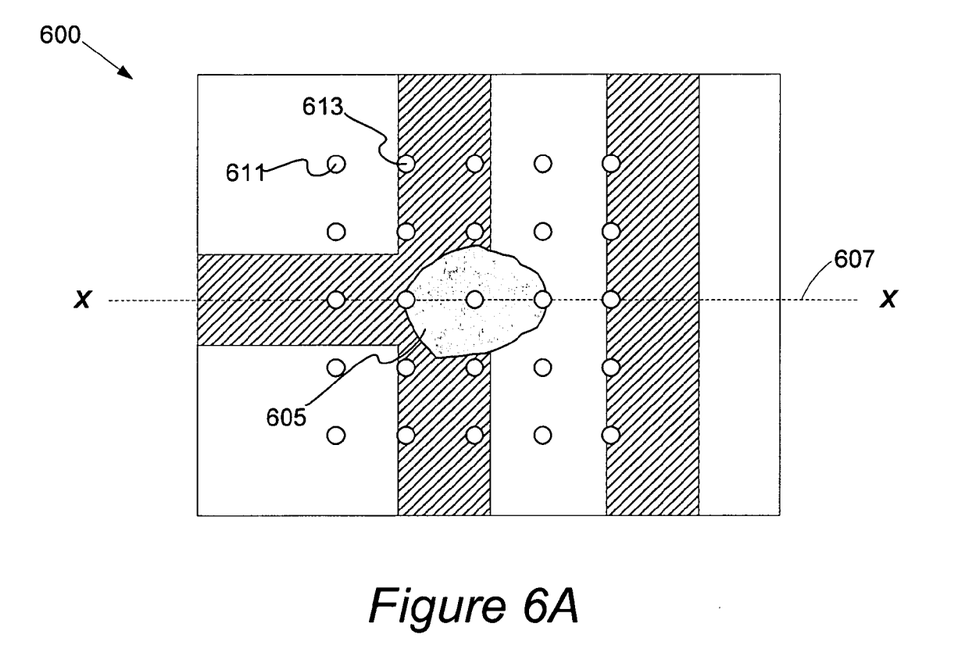
FIG. 6A illustrates a top view of a section of a semiconductor wafer showing an e-beam stepping grid pattern.
Figure 6B:
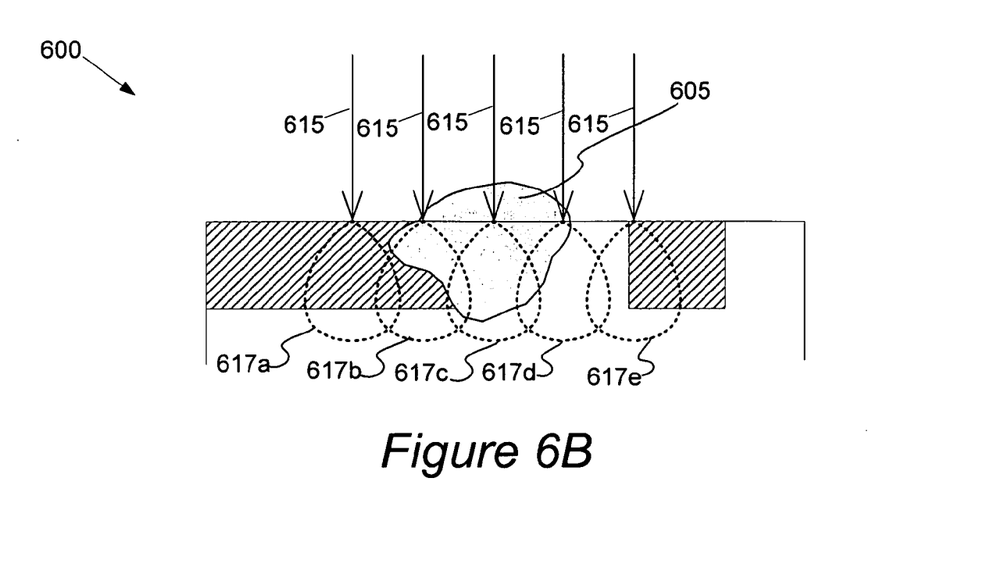
FIG. 6B illustrates a cross sectional view of the semiconductor wafer with e-beam stepping grid pattern of FIG. 6A, depicting the volume of semiconductor sampled.

A third method of e-beam inspection is stepping the e-beam. This method is similar to the first method described in which the e-beam is directed in only one area at a time, however, the e-beam is stepped several times over a larger sampling area. The e-beam is stepped in a pattern, typically a grid pattern, over the wafer surface. For example, FIG. 6A depicts a wafer sample 600, showing a five-by-five stepping grid pattern over the general area of a defect 605. Of course, any suitable sizes of grid may be utilized to inspect a defect, depending on the particular type and size of the defect. The grid points, wherein the e-beam impinges, may have any suitable size and be spaced apart any suitable distance for analyzing a defect. For example the grid points and corresponding e-beam diameters may be sized and spaces such that the resulting excitation volumes overlap or touch to thereby generate a complete image of the defect area (e.g., as illustrated in FIG. 6B). The e-beam is typically on only during the time that it is over each of the points in the grid. In this case, the e-beam is initially positioned over the point 611. The e-beam is then turned on and the emitted X-rays are detected. The e-beam is then turned off. Next the e-beam is positioned over point 613. The e-beam is then turned on and the emitted X-rays for this second point 613 are detected. This pattern is continued until the five-by-five matrix is complete.

FIG. 6B depicts a cross sectional view of the wafer sample 600 and defect 605 of FIG. 6A. E-beam 615 is shown impinging the area of the wafer surface with defect 605 at five of the twenty-five points of the stepping grid. This causes regions 617a through 617e within the sample to emit X-rays. Note that the e-beam 615 impinges each of these points at different times. The X-rays can be detected by any of the various methods described earlier, such as those illustrated in FIGS. 5A–5D. The resulting data is collected and combined to create a multidimensional X-ray image or map of the stepped region, which is described further below.

This third method of stepping the e-beam is more time consuming compared to the single point inspection and e-beam rastering methods. This is because stepping the e-beam typically requires turning on an off the e-beam and placement of the e-beam over each of the grid points. However, the stepping method allows for the collection of more differentiated data, thereby allowing for more accurate characterization and localization of defects compared to the other two e-beam sampling methods. That is, the sampling increments between the points of a stepping pattern can be chosen to optimize the coverage of a particular volume of wafer to be sampled. Conversely, when rastering, the e-beam is on during the entire scanning, creating overlapping sample volumes and collection of redundant data. The time it takes to perform e-beam stepping inspection varies broadly since it depends on the number of inspection points and the size of the inspection area.

All of the e-beam inspection methods described above can be used in accordance with the present invention. The third method of stepping the e-beam over the wafer sample is a preferred embodiment for the reasons stated above. A preferred method of stepping the e-beam is to step the e-beam in a grid pattern. It is noted, however, that the invention is not limited to this e-beam sampling method, or of the e-beam sampling methods described above. The invention can be applied to variations and combinations of these methods as well as any other suitable e-beam sample methods.

Resovling Elemental Composition of Defects

As described previously, X-ray emissions techniques can be used to determine the elemental composition of a sample. In the example used previously, an X-ray emission spectrum from a copper interconnect structure surrounded by silicon dioxide was shown (FIG. 2). This spectrum showed peaks from Cu Lα, Cu Kα, O Kα and Si Kα X-ray emissions. Each sampling from different parts of the interconnect structure will provide a unique spectrum. These spectra are used to determine the elemental composition of a portion of the wafer sample. These same X-ray emissions techniques can also be used to determine the elemental composition of defects. Combining these elemental analysis techniques with the spatial localization techniques will further characterize defects.

Figure 7A:
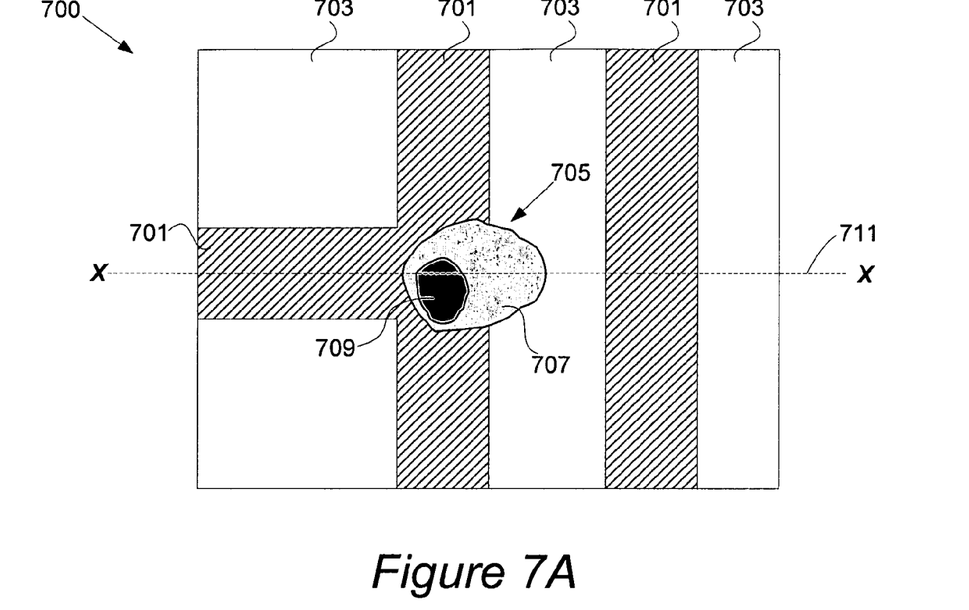
FIG. 7A illustrates a top view of a section of a semiconductor wafer with a defect comprised of two elements, carbon and aluminum.
Figure 7B:
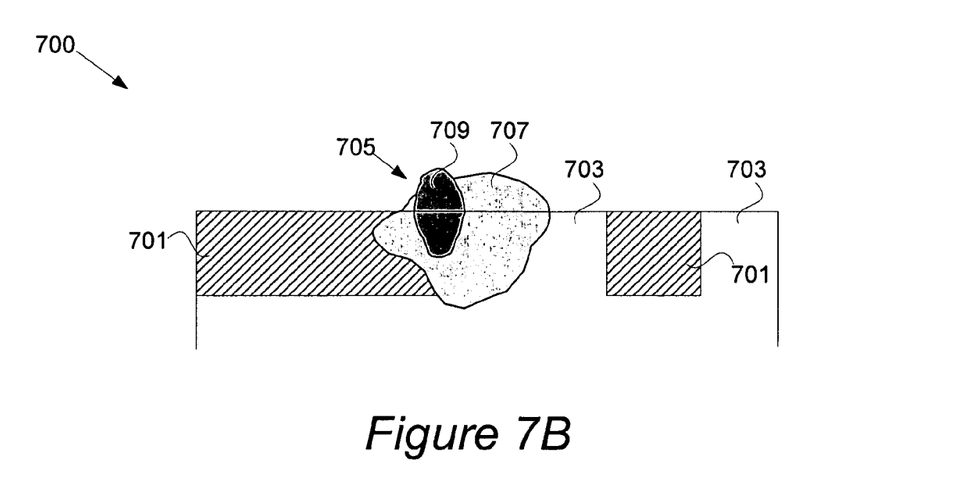
FIG. 7B illustrates a cross sectional view of the semiconductor wafer of FIG. 7A.

For example, FIGS. 7A and 7B illustrate a top view and a cross sectional view, respectively, of a wafer portion 700. The view FIG. 7B is a cross sectional view at line 711. Wafer portion 700 contains a particle defect 705, which lies on and within copper lines 701 and surrounding silicon dioxide 603. The defect 705 is comprised of two components, carbon 709 and aluminum 707, localized in different parts of the defect 705. Using X-ray emission techniques just described, the elemental composition of defect 705 (carbon and aluminum) can be determined.

To further characterize the defect 705, the spatial locations of the different elemental compositional components are determined by using any of the various methods described earlier, such as those illustrated in FIGS. 5A–5D. By combining the elemental composition and spatial data, the location of the carbon 709 and aluminum 707 portions with respect to the defect can be determined. This is in addition to the already determined spatial location of the defect with respect to the wafer. From this information, one could produce a multi dimensional X-ray image of the defect showing the locations of different elemental components of the defect. These elemental components can be shown using any of a number of standard imaging techniques. One technique may involve matching each element to a certain color. For example, blue could represent silicon, orange could represent copper, black could represent carbon and purple could represent aluminum. Or one could use a gray scale representation in which each element is represented by different shades of gray.

Creating Maps

Methods for detecting emitted X-rays from multiple perspectives, using different e-beam sampling techniques and determining the elemental composition of defects have been described. Focus will now be given to typical methods for creating the multiple perspective X-ray images, or maps, after the X-ray data is acquired. Other standard techniques not described can also be used in accordance with the present invention.

Figure 8:
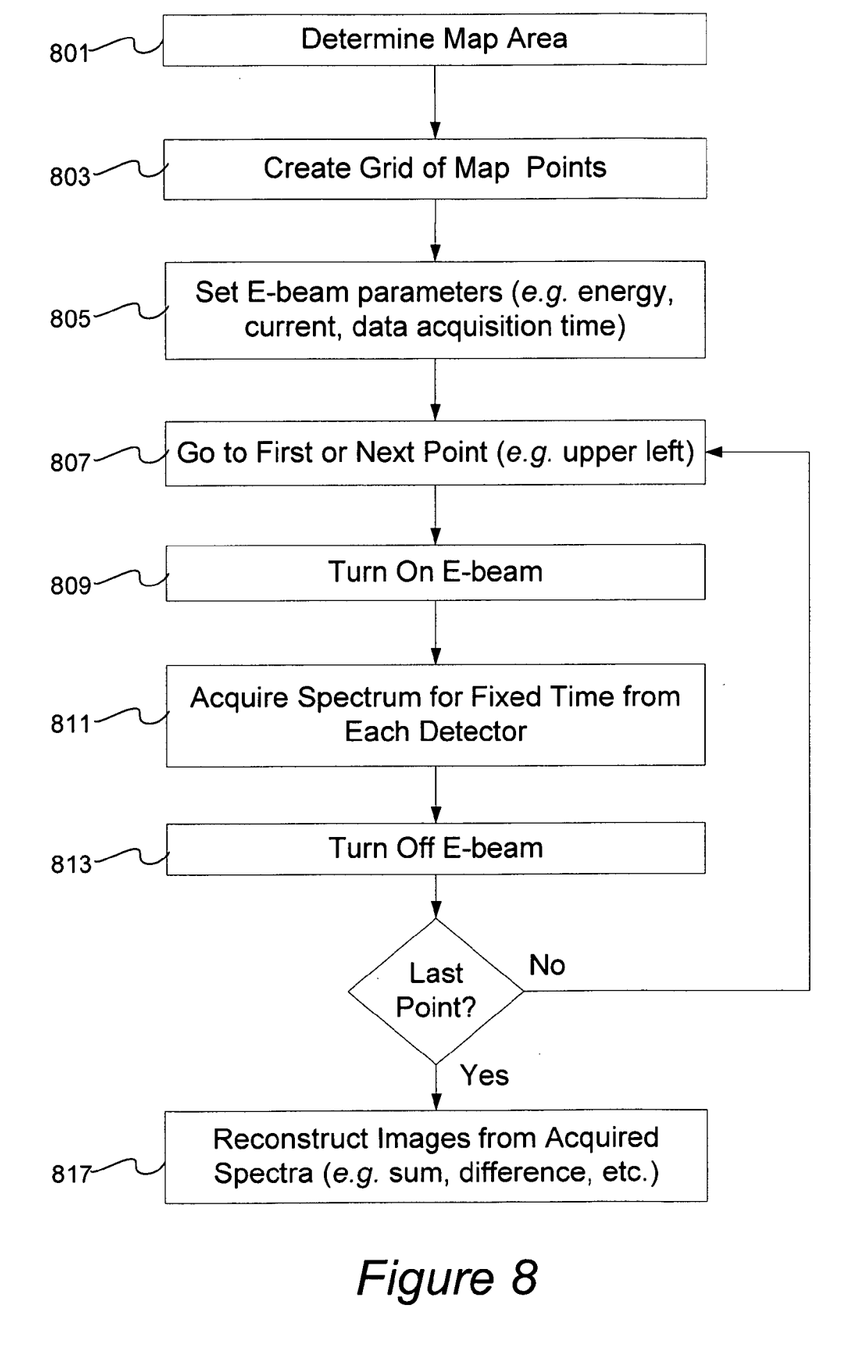
FIG. 8 is a flowchart illustrating a procedure for inspecting a semiconductor defect in accordance with the present invention.

As described previously, the elemental composition of the defect and the surrounding semiconductor material can be determined using spectral data. In practice, each time the e-beam is turned on and X-rays are detected from a certain angle or perspective, the X-ray spectrum from this perspective is collected and stored in a computer processor. FIG. 8 is a flow chart illustrating a procedure for forming a multi-perspective image based on the X-ray spectrum. Initially, the map area on the wafer or sample is determined in operation 801. The map area includes one or more defects, preferably one defect. For example, the map area may include any of the areas shown in FIGS. 4A, 6A, or 8A. The defect in the map area may have been found using any suitable inspection technique, such as an optical or scanning electron microscopy inspection technique. Once a defect is found, it is then desirable to image the defect so that the image (as described herein with respect to FIG. 8) may then be used with any further defect analysis procedures, such as automatic defect classification.

After the map area is determined, in operation 803 the map area is conceptually divided into a plurality of grid points, such as the grid points 611 and 613 of FIG. 6A. Each grid point corresponds to an e-beam diameter. E-beam parameters are then set in operation 805 and the e-beam is moved relative to the sample so that a first grid point is under the e-beam in operation 807. The e-beam parameters are selected to produce an excitation volume of X-ray emission around and under the first grid point. The e-beam parameters may include landing energy, beam current, and data acquisition time. Operations 805 and 807 may be interchanged and performed in a reverse order. The e-beam is then turned on so that it impinges upon the first grid point in operation 809. As discussed above, an excitation volume which emits X-rays as a result of the impinging e-beam is then produced at the first grid point. X-ray spectrum data is then detected and acquired by each detector in operation 811. The grid points are sized and spacing distance between each grid point are selected so that the resulting excitation volumes will result in a desirable resolution within the resulting image to facilitate analysis and/or classification of the defect.

The e-beam is then turned off in operation 813, and operations 809 through 813 are repeated for additional grid points. After the e-beam impinges on the last grid point, an image may be reconstructed from the acquired X-ray data from one or all of the detectors in operation 817. Alternatively, images may be constructed as each grid point is inspected with the e-beam.

For example, one can create an individual image, or map, for each element found in the spectra. These elements could then be associated with different screen colors. For example, one could use blue to represent silicon, orange to represent copper, yellow to represent tantalum and black to represent carbon-containing species. One image may be generated for each detector and its corresponding spectra obtained at each grid point. Then the computer processor can combine these images from the different grid points and different detectors into one image to create a final image will all the representative elements. Alternatively, one could use a gray scale whereby different shades are used to represent the different elements. The images may be combined in any suitable manner. By way of examples, the images may be summed together or subtracted from each other to obtain a final image. Alternatively, each image may be analyzed separately without combining them.

The images (or final combination image) generated from the X-ray spectra obtained from each grid point and each detector may then be analyzed for any suitable defect analysis purpose. In one application, an image which combines the X-ray spectrum from the different detectors at different perspectives at each grid point may be analyzed to determine the three dimensional nature of the defect. For instance, the image may contain shadowing, which shows that the defect is a particle or a recess. In another application, an image from a first detector at a first angle may be compared with an image from a second detector at a second angle, which is symmetrical to the first angle with respect to the defect to determine characteristics of the defect, such as symmetry. For instance, when shadowing is present within the first image and not the second image, one may determine that the defect is not symmetrical or homogenous. In contrast, if the two images contain identical shadowing or no shadowing, it may be determined that the defect is symmetrical or homogenous.

X-Ray Emissions Apparatus

Figure 9:
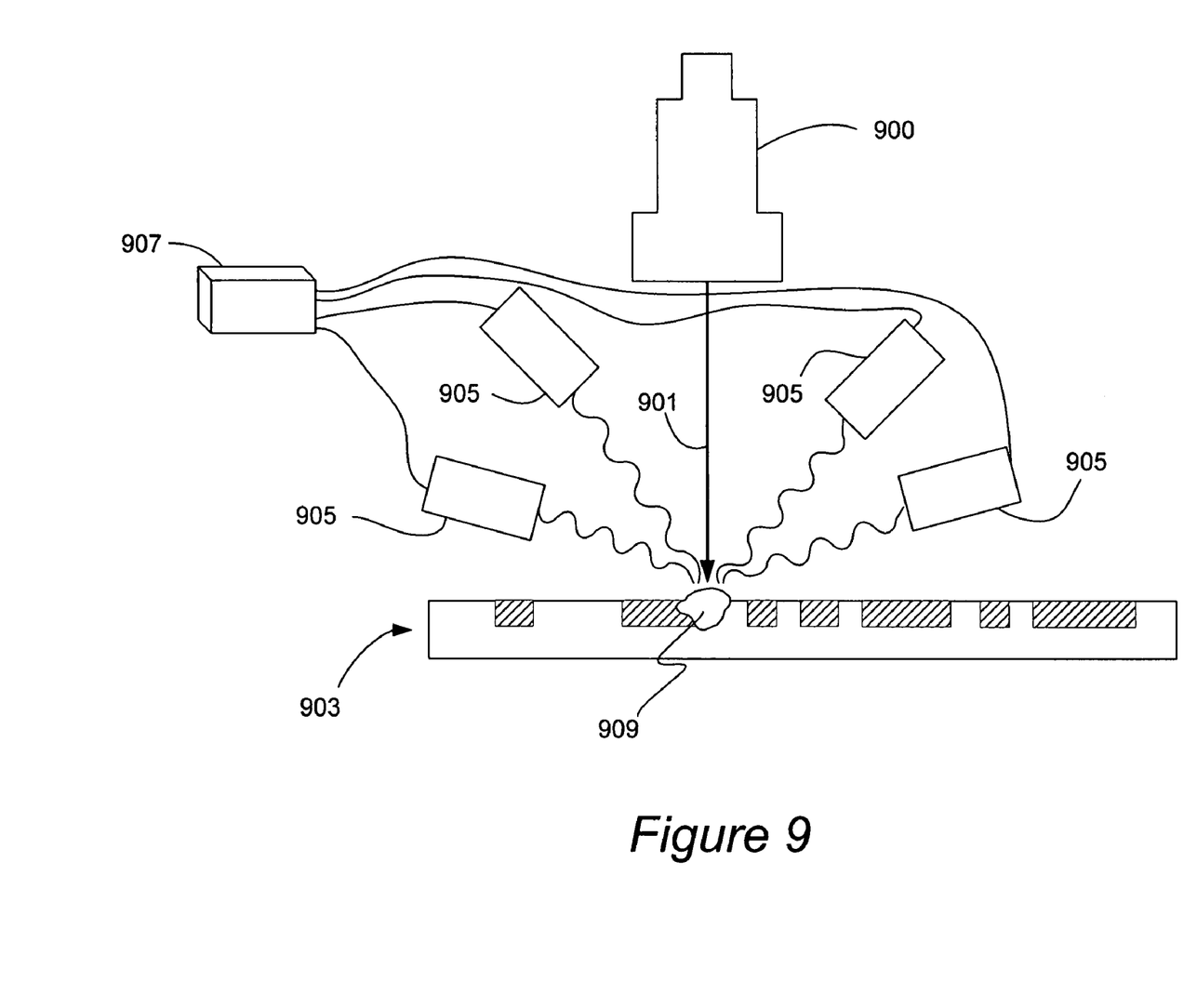
FIG. 9 illustrates an electron beam induced X-ray microanalysis test system according to one embodiment of the present invention.

Any suitable e-beam induced X-ray microanalysis system may be utilized to practice and/or implement the techniques of the present invention. An eV300 automated e-beam wafer inspection system available from KLA-Tencor Corporation of San Jose, Calif. may be used. FIG. 9 is a diagrammatic representation of a system utilizing an e-beam induced X-ray microanalysis test system according to one embodiment of the present invention. The system represented in FIG. 9 includes a beam generator 900, which directs an e-beam 901 at the sample 903. The sample 903 in the example depicted in FIG. 9 is a semiconductor wafer containing a particle defect 909. The spot size of e-beam may be any suitable size to resolve defects, preferably even very small defects. As described previously, the e-beam is preferably stepped over the general area in which a defect resides. At least two X-ray detectors are used to collect the X-rays emitted from the surface of the sample, although any suitable number of detectors may be used. The system in FIG. 9 includes four X-ray detectors 905 positioned at different angles above the sample.

Any suitable type of detector for measuring X-rays at specific energy levels may be used. One type of detector is an Energy Dispersive system (EDX), which collects photons in a wide spectrum of energies. EDX systems are capable of collecting a greater range of signals. As a result however, EDX detectors also collect photons having energies surrounding the characteristic photon energies. This causes EDX detectors to have lower signal to noise ratios. Another type of detector is a wavelength dispersive system (WDS) X-ray detector. Several suitable embodiments of WDS X-ray detectors are described further in co-pending U.S. patent application Ser. No. 09/695,726, filed 23 Oct. 2000, which application is incorporated herein by reference in its entirety.

In the system depicted in FIG. 9, each of the X-ray detectors is coupled with an analysis or processor unit 907. The analysis/processor unit 907 can be configured to analyze the data collected by the X-ray detectors 905, to generate X-ray maps/images from different perspectives and combine the X-ray maps/images to create spatially resolved images described previously. The analysis/processor unit 907 may take the form of any suitable processing or computing system, such as a workstation.

Although the foregoing invention has been described in some detail for purposes of clarity of understanding, it will be apparent that certain changes and modifications may be practiced within the scope of the appended claims. Therefore, the described embodiments should be taken as illustrative and not restrictive, and the invention should not be limited to the details given herein but should be defined by the following claims and their full scope of equivalents.

What is claimed is:

1. A method of inspecting a defect in or on a semiconductor wafer, comprising:
   directing a beam towards the surface of the semiconductor wafer wherein/whereon the defect resides to thereby emit X-rays;
   detecting the emitted X-rays with plurality of detectors positioned at a plurality of angles with respect to the wafer surface;
   collecting X-ray data from the detectors; and
   based on the X-ray data collected from the detectors at the plurality of angles, determining a location of the defect in three dimensions in relation to a plurality of different process layers of the wafer.

2. A method as recited in claim 1, wherein the detectors detect the emitted X-rays simultaneously.

3. A method as recited in claim 1, wherein an image is generated by combining the X-ray data from at least two X-ray emission energy spectra.

4. A method as recited in claim 1, wherein the defect resides fully within a sample volume.

5. A method as recited in claim 1, wherein the beam is stepped over an area where the defect resides.

6. A method as recited in claim 5, wherein the beam is stepped in a grid configuration.

7. A method as recited in claim 1, wherein the beam is rastered over an area where the defect resides.

8. A method as recited in claim 1, wherein the directed beam is an electron beam.

9. A method as recited in claim 1, wherein the directed beam is a focused ion beam.

10. A method as recited in claim 1, further comprising determining the elemental composition of the defect based on the collected X-ray data.

11. A method as recited in claim 1, wherein the semiconductor wafer comprises copper surrounded by dielectric material.

12. A method as recited in claim 11, wherein the detected X-rays are at least copper $K\alpha$ and copper $L\alpha$ X-rays.

13. A method as recited in claim 11, wherein the detected X-rays are at least copper $K\alpha$, copper $L\alpha$ and silicon $K\alpha$ X-rays.

14. A method of inspecting a defect in or on a semiconductor wafer, comprising:
   directing a beam towards the surface of the semiconductor wafer wherein/whereon the defect resides to thereby emit X-rays;
   detecting the emitted X-rays with a detector at a first angle with respect to the wafer surface;
   collecting X-ray data from the detector;
   directing a beam towards the surface of the semiconductor wafer wherein/whereon the defect resides to thereby emit X-rays;
   detecting the emitted X-rays with the detector at a second angle with respect to the wafer surface;
   collecting X-ray data from the detector; and
   based on the X-ray data collected at the first and second angles, determining a location of the defect in three dimensions in relation to a plurality of different process layers of the wafer,
   wherein the second angle of the detector with respect to the wafer surface is achieved by (i) moving the position of the detector to the second angle after collecting the X-ray data from the detector at the first angle or (ii) tilting the wafer to achieve the second angle after collecting the X-ray data from the first angle.

15. A method as recited in claim 14, wherein the detector detects the emitted X-rays at the first and second angles at different sampling times.

16. A method as recited in claim 14, wherein the detector detects emitted X-rays at a plurality of angles with respect to the wafer surface.

17. A method as recited in claim 14, wherein the second angle of the detector with respect to the wafer surface is achieved by moving the position of the detector after collecting the X-ray data from the first angle.

18. A method as recited in claim 14, wherein the second angle of the detector with respect to the wafer surface is achieved by tilting the wafer after collecting the X-ray data from the first angle.

19. A method as recited in claim 14, wherein using the X-ray data to spatially resolve the location of the defect is accomplished by generating an image based on the X-ray data.

20. A method as recited in claim 19, wherein the image is generated by combining the X-ray data from at least two X-ray emission energy spectra.

21. A method as recited in claim 14, wherein the defect resides fully within a sample volume.

22. A method as recited in claim 14, wherein the beam is stepped over an area where the defect resides.

23. A method as recited in claim 22, wherein the beam is stepped in a grid configuration.

24. A method as recited in claim 14, wherein the beam is rastered over an area where the defect resides.

25. A method as recited in claim 14, wherein the directed beam is an electron beam.

26. A method as recited in claim 14, wherein the directed beam is a focused ion beam.

27. A method as recited in claim 14, further comprising determing the elemental composition of the defect from the X-ray data collected at the first and second angles.

28. A method as recited in claim 14, wherein the semiconductor wafer comprises copper surrounded by dielectric material.

29. A method as recited in claim 28, wherein the detected X-rays are at least copper Kα and copper Lα X-rays.

30. A method as recited in claim 29, wherein the directed beam is a focused ion beam.

31. A method as recited in claim 29, further comprising determining the elemental composition of the defect from the collected X-ray data.

32. A method as recited in claim 29, wherein the semiconductor wafer comprises copper surrounded by dielectric material.

33. A method as recited in claim 32, wherein the detected X-rays are at least copper Kα and copper Lα X-rays.

34. A method as recited in claim 32, wherein the detected X-rays are at least copper Kα, copper Lα and silicon Kα X-rays.

35. A method as recited in claim 28, wherein the detected X-rays are at least copper Kα, copper Lα and silicon Kα X-rays.

36. A method of inspecting a defect in or on a semiconductor wafer, comprising:
    directing a beam towards the surface of the semiconductor wafer wherein/whereon the defect resides to thereby emit X-rays;
    detecting the emitted X-rays substantially, simultaneously at a plurality of angles with respect to the wafer surface with a single detector;
    collecting X-ray data from the detector; and
    based on the collected X-ray data that is detected at the plurality of angles, determining a location of the defect in three dimensions in relation to a plurality of different process layers of the wafer.

37. A method as recited in claim 32, wherein an image is generated by combining the X-ray data from at least two X-ray emission energy spectra.

38. A method as recited in claim 36, wherein the defect resides fully within a sample volume.

39. A method as recited in claim 36, wherein the beam is stepped over an area where the defect resides.

40. A method as recited in claim 39, wherein the beam is stepped in a grid configuration.

41. A method as recited in claim 36, wherein the beam is rastered over an area where the defect resides.

42. A method as recited in claim 36, wherein the directed beam is an electron beam.

43. An apparatus for inspecting a defect in or on a semiconductor wafer, comprising:
    a beam generator operable to direct a charged particle beam towards a structure;
    a plurality of detectors positioned at different angles with respect to the surface of the semiconductor wafer to detect X-rays from the structure in response to the charged particle beam; and
    a processor operable to:
        cause the beam generator to direct a beam towards the structure; and
        characterize one or more defects based on the detected X-rays from the plurality of detectors so as to spatially resolve a location of the one or more defects in three dimensions and in relation to a plurality of different process layers of the wafer.

44. An apparatus as recited in claim 43, wherein the characterizing operation is based on a ratio of a first X-ray intensity for a first material over a second X-ray intensity for a second material, wherein the first and second X-ray intensities are obtained from the detected X-rays from the scanned structure.

45. An apparatus as recited in claim 43, wherein the scanned structure is a portion of a interconnect structure in an integrated circuit device.

46. An apparatus as recited in claim 43, wherein the directed beam is an electron beam.

47. An apparatus as recited in claim 43, wherein the electron beam is stepped over an area of the sample surface.

48. An apparatus as recited in claim 43, wherein the electron beam is rastered over an area of the sample surface.

49. An apparatus as recited in claim 43, wherein the directed beam is a focused ion beam.

* * * * *

UNITED STATES PATENT AND TRADEMARK OFFICE
CERTIFICATE OF CORRECTION

| | | |
|---|---|---|
| PATENT NO. | : 7,202,475 B1 | Page 1 of 1 |
| APPLICATION NO. | : 10/796577 | |
| DATED | : April 10, 2007 | |
| INVENTOR(S) | : Anne L. Testoni | |

It is certified that error appears in the above-identified patent and that said Letters Patent is hereby corrected as shown below:

Column 9, line 6, delete "," after "to".

Column 10, line 55, change "resovling" to --resolving--.

In line 1 of claim 37 [column 15, line 48] change "32" to --36--.

Signed and Sealed this

Third Day of June, 2008

JON W. DUDAS
*Director of the United States Patent and Trademark Office*